US006664099B1

(12) United States Patent
Worrall

(10) Patent No.: US 6,664,099 B1
(45) Date of Patent: Dec. 16, 2003

(54) METHOD FOR THE PRESERVATION OF VIRUSES AND MYCOPLASMA

(75) Inventor: Eric Edward Worrall, Lampeter (GB)

(73) Assignee: Anhydro Limited, North Lincolnshire (GB)

( * ) Notice: Subject to any disclaimer, the term of this patent is extended or adjusted under 35 U.S.C. 154(b) by 0 days.

(21) Appl. No.: 09/980,698
(22) PCT Filed: May 3, 2000
(86) PCT No.: PCT/GB00/01524
§ 371 (c)(1), (2), (4) Date: Mar. 8, 2002
(87) PCT Pub. No.: WO00/66710
PCT Pub. Date: Nov. 9, 2000

(30) Foreign Application Priority Data

May 4, 1999 (GB) .......... 9909999
Nov. 12, 1999 (GB) .......... 9926698

(51) Int. Cl.[7] .......... C12N 1/04

(52) U.S. Cl. .......... 435/260; 435/235.1; 435/870; 435/948; 424/488; 424/211.1; 424/212.1; 424/214.1; 424/217.1; 424/218.1; 424/219.1; 424/264.1

(58) Field of Search .......... 435/235.1, 260, 435/870, 948; 424/484, 488, 489, 499, 211.1, 212.1, 214.1, 217.1, 218.1, 219.1, 264.1

(56) References Cited

FOREIGN PATENT DOCUMENTS

WO 96 40077 A * 12/1996

OTHER PUBLICATIONS

Kagumba, "Lyophilisation of $T_1$ broth culture vaccine of *Mycoplasma var. Mycoides*", Bulletin of Animal Health and Production in Africa, Vol 25, No. 2(1977), pp. 116–121.*

Languet et al. "Freeze–dried vaccine against rinderpest: stability and acitivty study", Comparative Immunology Microbiology and Infectious Diseases, Vol 8, Nos. 3–4(1985), pp 285–296.*

* cited by examiner

*Primary Examiner*—Jeffrey Stucker
(74) *Attorney, Agent, or Firm*—Bret E. Field; Bozicevic, Field & Francis

(57) ABSTRACT

A biologically-active material comprising a live virus or mycoplasma is preserved by a method of desiccation, without lyophilisation, in a matrix of glassy trehalose having a residual moisture content of not greater than 2%. The method comprises two vacuum drying stages. In a cycle time much shorter than a typical freeze drying process a virus or mycoplasma can be preserved to provide a material that can be rehydrated to give a vaccine having potency.

9 Claims, 1 Drawing Sheet

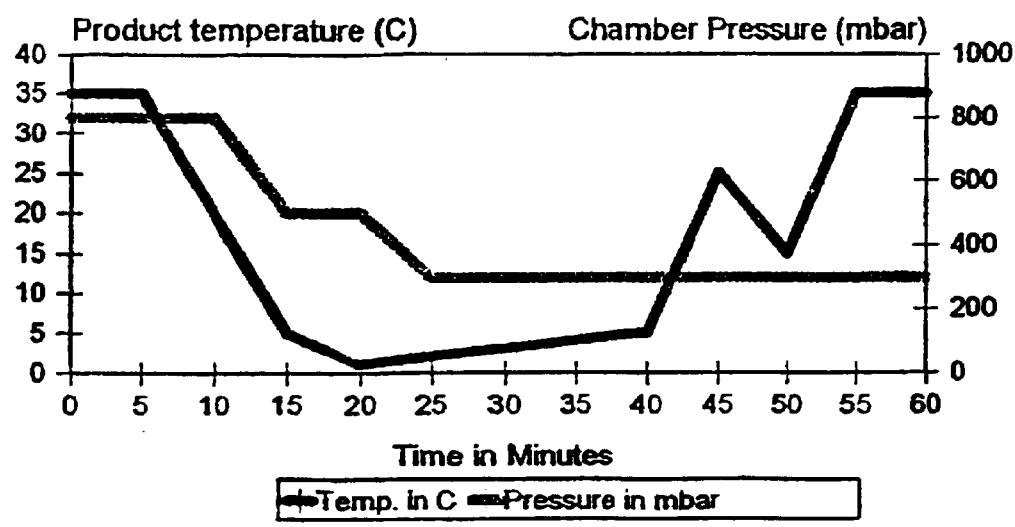
Fig. 1: Primary Drying Process Chart

METHOD FOR THE PRESERVATION OF VIRUSES AND MYCOPLASMA

The present invention relates to the preservation of viruses and mycoplasma. In particular, it relates to an ultra-rapid method by which such materials can be preserved using the disaccharide, trehalose. By this method, a long term preservation of viruses and/or mycoplasma can be achieved and, especially, living attenuated vaccines can be prepared.

The preservation of biodegradable materials by dehydration and osmoconcentration is a familiar and ancient technology. When the task of preserving sensitive biomolecules became necessary, simple drying by dehydration failed, as structural water was removed, causing subsequent denaturation and loss of vital activity. Cryopreservation in liquid nitrogen and lyophilisation have become the accepted methods for the long term preservation of sensitive biomolecules, the latter method being used extensively for the preservation of live attenuated vaccines.

Improved thermotolerance of freeze dried Rinderpest vaccine has been achieved by extending the secondary drying cycle, in order to reduce residual moisture (RM) levels to around 1%–2%. This entails long and high energy consuming operational cycles of up to 72 hours as described by Mariner, J. C. et al., Vet. Microbiol., 1990, 21, 195–209. Vaccines produced by this method are known and are distinguished from the standard vaccine by the name "THERMOVAX".

As mentioned above, these currently used processes are time consuming and involve high energy input. Furthermore, lyophilisation confers only a modest level of thermotolerance in the final product and refrigeration is still required to reduce deterioration during storage. This is a particular problem for live vaccines to be used in tropical climates since these lose potency with the unfortunate result that vaccination programs carried out in the field in tropical countries, where monitoring the "cold chain" is difficult, ultimately lead to vaccination of patients with substandard or, in some cases, useless vaccine.

During evolutionary natural selection, certain species of plants and animals acquired the remarkable and elegant ability to tolerate extreme dehydration, remaining dormant in hostile environments for very long periods of time and yet able to assume complete vital activity on rehydration. Examples include the resurrection plant *Selaginella lepidophya*, the brine shrimp *Artemia salina* (Clegg, J., J.Comp.Biochem.Physiol, 1967, 20, 801–809), the yeast *Saccharomvces cerevisiae* (Coutinho, E., Journal of Biotechnology, 1988, 7, 23–32) and the tardigrade *Macrobiotus hufelandi* (Kinchin, I. M., Biologist, 1995, 42, 4). Such organisms are termed cryptobiotic and the process by which they survive is known as anhydrobiosis. All species of animals and plants which display this ability contain the disaccharide trehalose ($\alpha$-D-glucopyranosyl-$\alpha$-D-glucopyranoside). Its presence generally in the order of 0.2 g/g dry cell weight in most cryptobionts enables them to resist extreme dehydration, high temperatures, X-rays and also in some species of tardigrades, pressures as high as 600 Mpa.

Colaco et al., Biotechnology, 1992, 10, 1007–1011, describe the benefit of rapid drying of biological materials using trehalose. This method mostly refers to the drying of restriction enzymes and immunoglobulins onto preformed solid matrices, such as cellulose fibres or onto the surfaces of plastic plates for diagnostic purposes such as ELISA or similar diagnostic applications in the laboratory. Problems arise, however, with these techniques when scaling up to industrial applications, such as large scale commercial vaccine production where much larger unit numbers and volumes have to be handled using mandatory aseptic techniques in partially sealed vials. To meet the operational requirements of large scale vaccine production, where unit volumes from 1.0 ml upwards and production batches of 20 litres are typical, a different strategy is required to remove that volume of water in an economically acceptable time. Drying at atmospheric pressure even at the highest physiologically tolerated temperatures would require an unacceptably long time to remove water quickly enough from partially stoppered vaccine vials and would inevitably result in denaturation and loss of potency.

The present invention is concerned with a method of preservation of viruses or mycoplasma using trehalose under conditions which cause water to be removed while, at the same time, allow the biological integrity of the material to be maintained.

Accordingly, the present invention provides a method of preserving a biologically-active material comprising a live virus or mycoplasma which method comprises the steps:

(i) mixing an aqueous suspension of the biologically-active material with a sterile aqueous solution of trehalose to give a trehalose concentration in the mixture in the range of from 0.2 to 10% w/v;

(ii) subjecting the mixture to primary drying, for 30 to 60 minutes, at a pressure of less than atmospheric and at a temperature initially no greater than 37° C., and which is controlled not to fall to 0° C. or below and which finally is no greater than 40° C. to form a glassy porous matrix comprising glassy trehalose having a residual moisture content of not greater than 10% and containing, within the matrix, desiccated biologically-active material; and (iii) subjecting the glassy porous matrix of step (ii) to secondary drying for 10 to 30 hours at a pressure not greater than 0.1 mbar and at a temperature which finally is in the range of from 40 to 45° C. to form a trehalose matrix having a residual moisture content of not greater than 2% containing, within the matrix, desiccated biologically-active material.

By using the method of the invention it is possible to produce a live vaccine with, compared to prior art methods, enhanced biological characteristics and distinct commercial advantages. Vaccines prepared using the method of the invention are dried much more quickly than those using conventional freeze drying procedures. For instance, the method of the invention can be used to dry trehalose/biologically-active material mixtures to a moisture content of about 10% in less than one hour. Further dehydration to a residual moisture content of about 1–2% can be achieved in less than 30 hours, for instance about 20 hours, compared to a period of 50 hours by conventional freeze drying procedures. Furthermore, damage caused by solute concentration is minimised according to the present invention and particularly damaging ice crystallisation is avoided. The thermostability of the biologically-active material preserved in the trehalose glassy matrix is greater than that of materials preserved by prior art methods and, thus, the necessity of the "cold chain", which is a serious constraint with conventional freeze-dried vaccine, is minimised. The product of the present invention can be exposed to high ambient temperatures, e.g., up to about 45° C., for prolonged periods without any substantial loss of biological activity. In addition to these and other advantages of the present invention the product of the method exhibits instantaneous "flash solubility" upon rehydration.

The method of the present invention is suitable for achieving the long term preservation of viruses and mycoplasma. In particular, it can be used to preserve highly labile live attenuated viral components and mycoplasma components that can be rehydrated to form vaccines. Examples of such biologically-active materials that can be preserved according to the method of the invention include:

Family: Paramyxoviridiae
Subfamily: Paramyxovirinae
Genera: Parainfluenza virus group Measles, Rinderpest, canine
distemper, Peste des Petits Ruminants (PPR)
Paramyxovirus: mumps virus (Mumps)
Genus: Rubivirus, Rubella (German Measles)
Genus: Flavivirus, Yellow fever virus (Yellow Fever)
Genus: Rhabdoviruses, Lyssaviridiae (Rabies virus)
Picoma viruses (Polio virus)
Newcastle Disease virus
Mycoplasma: *Mycoplasma mycoides* (Contagious Bovine Pleuropneumonia)

Brucella abortus: Strain 19 vaccine

Chlamydia: *Chlamydia psittaci* (Enzootic abortion)

Coccidia: *Toxoplasma gondii* (Toxoplasmosis)

According to the method of the present invention, the biologically-active material to be preserved is prepared as a suspension in an appropriate aqueous medium. In the case of a virus, it may be that this will need to be cultured, for instance in vero cells, in an appropriate culture medium, and then harvested prior to suspension in order to provide a useful concentration of material. Typically, the aqueous suspension of biologically-active material will be pH adjusted, for example by the addition of an alkali, to a pH in the range of from 7.0 to 7.8 especially about 7.4.

Trehalose is one of the most stable and chemically non-reactive disaccharides. It has an extremely low bond energy of less than 1Kcal/Mol making the dimer structure very stable. It does not undergo caramelisation unless heated severely, nor does it cause the Maillard reaction with proteins or peptides. The natural di-hydrate structure containing two water molecules enables unusual flexibility around the disaccharide bond which possibly permits a closer association with tertiary structured biomolecules. It is not hygroscopic yet exhibits “flash solubility” on hydration, a property particularly useful for dried vaccines.

The aqueous suspension of the biologically-active material is mixed with a sterile aqueous solution of trehalose and the mixture will be prepared such that it will have a trehalose concentration of from 0.20% to 10% w/v, preferably 2 to 10% and more preferably from 2.5 to 8% w/v. Within the range of trehalose concentrations, the actual concentration used will, in general, depend on the unit size of the biologically-active material. Less trehalose is required for small virus particles than for large cells.

The sterile aqueous trehalose/biologically-active material mixture is subjected to a vacuum drying procedure involving a primary drying step followed by a secondary drying step. Preferably, a conventional freeze drying apparatus (e.g., such as manufactured by EDWARDS, CHRIST, USIFROID or SAVANT) is used for the drying procedure in order to provide a controlled environment for the critical stages in the method. It is emphasised, however, that if such an apparatus is used freeze drying conditions are not employed and the material is not subjected to freeze drying. The drying procedure comprises two drying stages, a primary drying stage in which the residual moisture content of the material is reduced to a value of not greater than 10% and a secondary drying stage in which the residual moisture content of the material is reduced further to a value not exceeding 2%.

In the primary drying stage the initial temperature of the drying apparatus will be such as to ensure that the temperature of the trehalose mixture will not be greater than 37° C. and will preferably be 37° C. in order to prevent any loss of biological activity at this stage in the method. As water is evaporated off the mixture, the temperature of the mixture falls. The desiccation is, however, carried out to ensure that no freezing or sublimation from ice occurs as is normally experienced in conventional freeze drying procedures, i.e., the temperature of the product during this stage of the drying process is controlled not to fall to 0° C. or below and is typically controlled not to fall below 4° C. The pressure is reduced below atmospheric pressure, preferably to a value of from 800 to 300 mbar.

The primary drying stage is continued for a period of time, between 30 and 60 minutes, during which time the temperature of the trehalose mixture initially falls as water is evaporated off and then rises. When a temperature (under the reduced pressure employed) of about 25° C. is reached during this procedure the trehalose forms a glassy matrix comprising glassy trehalose and containing the biologically-active material which is in a desiccated or partially desiccated state. The primary drying stage is completed when the moisture content of the glassy matrix has reached 10% or below and it is essential, at this critical stage in the procedure, that the temperature is not allowed to exceed 40° C. If the temperature at the end of the primary drying stage does exceed 40° C. the biologically-active material will sustain damage.

The product obtained from the primary drying stage is then subjected to a secondary drying stage, preferably without removal from the drying apparatus used for the primary drying stage. In the secondary drying stage the glassy matrix obtained from the primary drying stage is further dehydrated under a reduced pressure, not exceeding 0.1 mbar. Currently-available specialised apparatus has the ability to operate at extremely low pressures, for instance below 0.001 mbar. However, very good results have been obtained according to the present invention using reduced pressures for the secondary drying stage in the range of from 0.001 to 0.1 mbar, typically from 0.01 to 0.1 mbar. The secondary drying stage is continued for a total period of time in the range of from 10 to 30 hours, preferably 20 to 30 hours.

As mentioned above, the temperature of the glassy matrix at the end of the primary drying stage does not exceed 40° C. During the secondary drying stage the temperature of the matrix may rise slightly to a final temperature, at the end of the drying procedure, of from 40° C. to 45° C. The trehalose matrix, at the end of the secondary drying stage will have a residual moisture content of 2% or less, preferably 1% or less in order to ensure a very high degree of thermostability in the product. At such residual moisture contents the final temperature in the drying process should not be higher than 45° C. since the desiccated biologically-active material in the matrix may undergo some degree of destruction above 45° C. Preferably, the temperature of the product at the end of the secondary drying stage will not exceed 44° C.

It has been found, through experimentation that there is some benefit in controlling the temperature of the matrix, during the secondary drying stage, such that it is maintained at about 37° C. for a period of from 15 to 17 hours and then raising this gradually (for instance by 0.5 to 1° C. per hour), over the remaining secondary drying time to a final temperature within the range of 40° C. to 45° C.

The glassy trehalose matrix produced according to the method can be rehydrated very quickly in an appropriate aqueous medium, typically sterile distilled water, to produce a vaccine for use in a very short period of time.

The preparation of the vaccine and the operating procedure using a freeze dryer for the desiccation of viruses, such as Rinderpest and Peste des Petits Ruminants viruses, and mycoplasma without a lyophilisation step involving sublimination from ice, exploits the unique property of the disaccharide trehalose to protect tertiary macromolecules during desiccation.

Compared to conventional freeze-drying procedures the method of the invention offers the following benefits:

It provides a high level of virus protection, employing a relatively short, simple procedure, e.g., a 25 hour production cycle, thus reducing production cycle time and energy costs.

Basic drying equipment is all that is required, although sophisticated microprocessor controlled freeze dryers can also be used, but are not strictly essential.

The method is tolerant of power interruption, unlike lyophilisation where even a short power failure can cause product meting, leading to unacceptable loss of virus.

Oral vaccination with some attenuated strains of virus has in the past been difficult to achieve because of the loss of epitheliotropism. Both oral and intranasal vaccination would be useful and appropriate for many applications because they mimic the natural route of droplet infection, generating a cascade of protective mucosal immunity, with IgA and humoral IgG2a T helper-cell type 1 response. It would be easy to administer such routes of vaccination and these would be applicable in the event that a suitable vaccine is prepared. A vaccination procedure with live attenuated strains mimicking the natural route of infection induces a more comprehensive sero mucous and cell mediated immunity. According to a further aspect the present invention provides a method of making a vaccine for oral or intranasal use which comprises preparing a glassy matrix of trehalose containing desiccated virus according to the above described method, combined with a suitable positively-charged, biocompatible, water-soluble adjuvant, and rehydrating the glassy matrix with an appropriate aqueous composition. According to a preferred embodiment of this aspect of the invention the vaccine for oral or intranasal vaccination is an MMR vaccine. Since the current paediatric MMR vaccine is prepared by conventional freeze drying technology and is injected into the patient subcutaneously, an oral or intranasal vaccine would give great benefits.

EXAMPLES

Example 1

A paramyxovirus Rinderpest RBOK attenuated vaccine strain was grown in secondary calf kidney cells for 10 days at 37° C. The virus suspension was harvested and clarified by centrifugation at 1000 rpm in a refrigerated centrifuge.

A sterile excipient containing 10% w/v trehalose and 5% lactalbumin hydrolysate was added at a ratio of 1:1 with the clarified virus fluid at 4° C.

The excipient/virus mixture 1.0 ml of this was aliquoted into sterile 10 ml neutral glass vials which were then partially stoppered with sterile dry butyl rubber stoppers.

The vials were placed on the shelf of the freeze drying chamber and the temperature of the product was raised to 37° C.

The condenser was started and the condenser temperature allowed to stabilise at −60° C.

The vacuum pump was started and the chamber containing the product was evacuated to a pressure of 800 mbar and the product gently degassed for 30 minutes to avoid sputtering whilst carefully checking the product temperature to avoid evaporative freezing. By maintaining a pressure gradient between the drying chamber and the refrigerated condensor 75% of the water vapour was driven over to the condenser in the first 30 minutes.

The pressure was then lowered to 500 mbar and a structured metastable glassy matrix was formed. The pressure was then further reduced to 0.10 mbar and maintained for 30 minutes.

The vials were stoppered and sealed under a final vacuum of 0.01 mbar and capped with aluminium closures.

Virus titre before drying: $10^4$TCID/50/ml

Virus titre after drying: $10^4$TCID/50/ml

The product matrix was flash soluble in distilled water. This example shows that the potency of the virus is substantially unaffected by the treatment employed in the primary drying stage of the method of the invention. It further illustrates the possibility of dehydrating the virus, to prepare viral vaccines, on an industrial scale.

Example 2

Materials and Methods
Preparation of the RP and PPR Vaccine Cultures

Peste des petits ruminants (PPRV 751/1) and Rinderpest (RBOK) strains were grown initially using vero cells in Glasgow modification Eagles medium (GMEM) supplemented with 10% tryptose phosphate broth (TPB, Difco) and 10% foetal calf serum (FCS) as follows:

Vero cells were seeded into 5×150cm$^2$ plastic flasks at a cell concentration of 287,000 cells/ml, 60 ml per flask. Two flasks were inoculated with 0.5 ml PPR virus suspension at a multiplicity of infection of 0.03 virus particles/cell. Two flasks were similarly inoculated with RP virus. One flask remained uninoculated as a control.

The flasks were incubated at 37° C. in 5% $CO_2$ and cells examined daily for development of cytopathic effects (cpe). On day 4 the GMEM medium was replaced with Hanks lactalbumin yeast extract (Hanks LYE), containing 2% FCS and 0.1% trehalose dihydrate. On day 6 the cpe was approximately 80% and the virus harvests were pooled, frozen and stored at −20° C. The control flask remained in the incubator for 10 days, and proved to be free from contamination or cell degradation, with no obvious sign of adventitious agents.

Dehydration Procedure

The dehydration procedure used can be considered to consist of two main components similar to lyophilisation: primary drying and secondary drying. The fundamental difference from lyophilisation is that the product is not frozen and drying is by simple dehydration, not sublimation from ice.

The pooled virus suspensions were thawed and diluted 1:1 with a sterile 5% w/v aqueous solution of trehalose dihydrate, thus giving a final concentration of 2.5% w/v trehalose in the mixture. One ml volumes were distributed into each of 5 ml vaccine vials and partially sealed with dry vented butyl rubber inserts. This operation was carried out at room temperature, in a laminar air flow biohazard cabinet and observing strict aseptic precautions.

Primary Drying

The dehydration process was carried out using an Edwards Supermodulyo freeze dryer with precise control over chamber pressure, condenser pressure, shelf and product temperatures. The freeze dryer was prepared in advance before loading the shelf chamber with the vials containing the product. The shelf temperature was raised to 40° C. and the condenser temperature was allowed to reach the operational limit of −40° C. Vials were then placed on the shelves and the contents allowed to reach 35° C. The chamber door was closed with the macro and micro air admittance valves fully opened and the vacuum pump switched on with full gas ballast. The pressure in the chamber was adjusted to 800 mbar by carefully closing the macro air admittance valve. The pressure in the condenser was maintained at 500 mbar in order to produce a pressure gradient between the chamber and condenser and this provided the driving force to induce water vapour to flow from the product surface to the condenser. Partial closure of the vials with the stoppers also had the beneficial effect of throttling the aperture thus increasing the pressure still further at the product surface. It was noticed that the partially closed vials dried quicker than the fully open ones containing the temperature recording thermocouples.

The change in the temperature of the product with time and the change in the chamber pressure with time during the primary drying stage are shown in the attached Figure. As can be seen in the Figure, evaporation started immediately as indicated by the fall in product temperature. The product temperature was controlled primarily by carefully closing the macro air admittance valve during the first 15 minutes, and thereafter by manipulation of the micro air admittance valve, making sure not to allow the product to freeze. Maintaining a temperature around 1–2° C. caused by evaporative cooling, increased the evaporation rate so that 90% of the water had evaporated within one hour and the product temperature began to rise to match the shelf temperature. As dehydration proceeded a critical point was reached after 40 minutes when there was a sudden rapid rise to 25° C. followed within seconds by a sudden fall in product temperature to 15° C. This was accompanied by a dramatic bubbling of the product.

Secondary Drying

A further batch (batch 2) of the live attenuated Rinderpest strain (RP) was prepared and subjected to primary drying for 1 hour as described above. This was then subjected to a period of secondary drying where the temperature was raised over a period of a further 17 hours to a final product temperature of 42.4° C. and a pressure of 0.06 mbar, with gas ballast fully closed. This had the effect of reducing the residual moisture content of the material to approximately 0.72%.

A further batch (batch 2) of the live attenuated Peste des petits ruminants strain (PPR) was prepared and subjected to primary drying for 1 hour as described above. This was then subjected to a period of secondary drying. The secondary drying was stopped after 2 hours at a product temperature of 42.8° C. and a chamber pressure of 0.06 mbar. The product, after this short secondary drying procedure, had a residual moisture content of 5.36%.

The Test for Thermostability

Samples from batch 2 of each of PPR and RP prepared as described above were stored at 4° C., 25° C., 37° C. and 45° C. Three vials from each storage temperature were taken for virus titration on days 0, 3, 7, 10 and 14-post incubation. The geometric mean of the three vials was considered as the residual virus titre for each batch type at each temperature for the specified period of incubation (Tables 3 and 4).

Virus Titrations

These were carried out to determine the efficiency of the ultra rapid one hour dehydration as assessed by the degree of protection induced by the trehalose glassy state. The virus titrations were performed as described in the standard operating procedures for Rinderpest vaccine described by Mark, M. Rweyemamu et al., in FAO Animal Production and Health Paper, 1994, No. 118. (NB FAO is the Food and Agriculture Organisation of the United Nations). Note: The main body for the regulation and co-ordination of animal vaccine quality is The Office International Epizooties (OIE). The OIE standard for potency for RP is $10^{2.5}$ $TCID_{50}$ s/dose and for PPR is $10^3$ $TCID_{50}$ s/dose (where TCID is the tissue culture infective dose). In the Tables 1, 2, 3 and 4 below the virus titres are expressed as X $\log_{10}$ $TCID_{50}$/ml where "X" is the figure shown under Test 1, 2 and 3 in each of the Tables.

Results and Discussion

The results obtained from paired samples of RP and PPR vaccine dried for one hour, using the method described above, in comparison with a control sample of lyophilised vaccine and also with the parent untreated virus pool containing 2.5% trehalose were as depicted in tables 1 and 2. The excipient containing 2.5% trehalose gave good protection of RP virus following the rapid dehydration at 37° C. under conditions of reduced pressure at 800 mbar with the loss following drying of 0.45 $\log_{10}$ $TCID_{50}$/ml.

TABLE 1

Rinderpest virus titration results after primary drying

| Substance tested | Test 1 | Test 2 | Test 3 |
| --- | --- | --- | --- |
| Virus pool + 2.5% Trehalose | 5.7 | 5.9 | 5.8 |
| Virus pool + 2.5% Trehalose dried at 37° C. for 1 hour | 5.0 | 5.7 | 5.35 |
| Lyophilised Reference Vaccine | 4.8 | 4.8 | 4.8 |

The protection of the PPR virus in the same excipient was excellent with only the loss of 0.15$\log_{10}$ $CID_{50}$/ml following drying.

TABLE 2

Peste des petits ruminants virus titration

| Substance tested | Test 1 | Test 2 | Test 3 |
| --- | --- | --- | --- |
| Virus pool + 2.5% Trehalose | 5.0 | 4.9 | 4.95 |
| Virus pool + 2.5% Trehalose dried at 37° C. for 1 hour | 4.9 | 4.7 | 4.8 |
| Lyophilised Reference Vaccine | 4.9 | 4.9 | 4.9 |

The incorporation of a secondary phase in the dehydration process clearly has a marked effect on the thermotolerance of the product. This is demostrated by the fact that the RP batch 2 which was subjected to 17 hours of secondary drying lost only log 1.9 TCID/50/ml after two weeks at 45° C.

TABLE 3

Thermostability test of Rinderpest Batch 2

| | Virus titre after storage at various Temperatures | | | |
| --- | --- | --- | --- | --- |
| Day of Incubation | 4° C. | 25° C. | 37° C. | 45° C. |
| 0 | 4.97 | 4.97 | 4.97 | 4.97 |
| 3 | 4.83 | 4.70 | 4.10 | 3.80 |
| 7 | 4.83 | 4.63 | 4.17 | 3.37 |
| 10 | 4.80 | 4.57 | 4.10 | 3.30 |
| 14 | 4.87 | 4.30 | 3.83 | 3.03 |

On other hand a PPR batch 2 which underwent only two hours of secondary drying had no detectable virus after 14 days of incubation at 45° C.

TABLE 4

Thermostability test of PPR Batch 2

| Day of Incubation | Virus titre after storage at various Temperatures | | | |
|---|---|---|---|---|
| | 4° C. | 25° C. | 37° C. | 45° C. |
| 0 | 5.40 | 5.40 | 5.40 | 5.40 |
| 3 | 5.33 | 4.80 | 4.57 | 3.90 |
| 7 | 5.33 | 4.77 | 4.40 | 2.70 |
| 10 | 5.40 | 4.77 | 3.97 | 2.50 |
| 14 | 5.27 | 4.50 | 3.60 | 0.00 |

The dehydration of Rinderpest and PPR viruses using the anhydrobiotic procedure described, produced a glass-like, honeycombed structure of approximately 10% residual moisture within one hour. It is hypothesised that the observed exotherm after 40 minutes drying, might indicate the glass transition temperature of the trehalose excipient under reduced pressure where the trehalose changes from a liquid and forms a metastable glass (see Robert J. Williams and A. Carl Leopold, The glassy state in corn embryos, *Plant Physiol.*, 1989, 89, 977–981). The product in this state with a residual moisture content of about 10% had a microcrystalline structure and exhibited dramatic "flash solubility" on rehydration with diluent. Accelerated thermostability tests on the product at 5.36% residual moisture caused unacceptable deterioration as evidenced by huge loss of virus titre (Table 4).

The excipient containing half strength Hanks LYE, 1% FCS and 2.5% w/v trehalose was sufficient to protect both RP and PPR viruses during the one hour, ultra rapid dehydration, when the residual moisture content was rapidly reduced to 10% (Tables 1 and 2).

Exposure to 45° C. for 14 days at 5.36% moisture destroyed the virus (Table 4). However, extension of the secondary dehydration for 17 hours had the expected effect of further reduction of the residual moisture (to less than 1%), thereby conferring increased thermostability (Table 3).

The drop in titre of log 1.9 TCID50/ml after exposure to 45° C. for 14 days, whilst maintaining a minimum titre of $Log_{10}3.03$ $TCID_{50}$/ml compares favourably with the expected fall in titre found in the current lyophilised "thermostable" (Thermovax) vaccines. The complete loss of virus in PPR batch 2 which underwent only 2 hours of secondary drying and then similarly exposed to 45° C., highlights the damaging effect of a high residual moisture content and emphasises the necessity of extending the secondary drying to ensure a low residual moisture content.

Example 3

Peste des Petits Ruminants (PPR) virus was propagated in vero cells in GMEM medium (Sigma No. G6148) containing 10% foetal bovine serum and 10% tryptose phosphate broth (Difco). The cells were propagated in 150 cm² flasks at a concentration of $26 \times 10^4 - 28 \times 10^4$ cells per ml adding 60 ml of cell suspension per flask.

Each 150 cm² flask was inoculated with sufficient PPR seed virus at a multiplicity of infection (MOI) of $10^{-3}$ virus particles/cell.

On day 4 post inoculation when early cytopathic effects (CPE) is noted the medium was replaced with Hanks lactalbumin yeast extract containing 2% foetal calf serum with 0.1% trehalose dihydrate (in place of glucose). This was to reduce the solute concentration and minimise osmotic stress during subsequent dehydration and to remove reducing sugars, such as glucose, which can contribute to the Maillard reaction which during dehydration can denature nucleoproteins.

On day 6 post inoculation, the cpe was 80–90%, the virus fluid was harvested and frozen overnight. The frozen fluid was thawed to liberate endogenous virus and stored at −20° C.

The thawed virus fluid was mixed with 16% w/v sterile aqueous trehalose dihydrate (DFS Ltd) in a 1:1 ratio to give a final concentration of trehalose of 8% in the virus excipient mixture.

One ml volumes of the virus excipient mixture were distributed into sterile 5 ml vaccine vials (1 ml of moisture into each vial) and the vials were partially stoppered with vented dry butyl rubber stoppers (freshly dried at 130° C. for 3 hours). The dehydration was carried out using an Edwards Super Modulyo freeze dryer.

The freeze dryer was prepared in advance before loading the shelf with the vials. The condenser was switched on and the condenser temperature was allowed to reach the operational limit of 40° C. The shelf heating was switched on and the shelf temperature was set to 40° C. The condenser door and the drain valve were closed and the vacuum pump switched on with full gas ballast. When the shelf temperature reached 40° C. the vials were loaded onto the shelf and a temperature thermocouple was inserted into a vial on each shelf and the chamber door closed with the macro and micro air admittance valves fully open.

When the temperature of the contents of the vials reached 35° C. the macro air admittance valves was partially closed to achieve a pressure of 800–900 mbar. During the first 15 minutes the excipient in the vials, which contained dissolved $CO_2$ from the bicarbonate in the medium, was gently degassed. During this phase access of trehalose to the virus lipid membrane could occur.

The macro air admittance valve was further closed to reduce the pressure down to 500 mbar. The temperature of the excipient in the vials was allowed to fall to approximately 4.0° C., indicating that evaporative cooling was taking place. The micro air admittance valve was carefully closed, while monitoring the excipient temperature, to stabilise the temperature around 4.0° C. This being the most critical phase in the operation, care was taken to avoid sputtering andlor a too rapid evaporation which would result in the freezing of the product. Sterile air was metered into the chamber to provide a pressure gradient to encourage the flow of water vapour to the condenser. The product temperature throughout was maintained at 4° C. by careful control of the micro air admittance valve. After maintaining the temperature of the product in the range of about 4° C. for 20 to 30 minutes the micro air admittance valve was slowly closed while taking care to maintain the product temperature of about 4° C. and a chamber pressure of 300 mbar. At this stage the product volume was considerably reduced to a syrupy consistency. The micro air valve was, by this time, fully closed.

After approximately 40 minutes from the beginning of the primary drying procedure the product temperature was seen to rise. After 45 minutes the bulk of the water in the excipient had been evaporated and the product expanded into a microcrystalline honeycomb structure accompanied by a sudden exotherm of approximately 15° C. as the trehalose vitrified into a metastable foamed glass matrix. Following this the temperature of the product fell as further moisture in the product evaporated to a give a product having a final moisture content of 10%.

With both macro and micro admittance valves closed and vacuum pump gas ballast valve closed, drying was continued overnight, at a chamber pressure of 0.1 mbar, during which time the product temperature reached 40° C., the temperature of the shelf in the chamber. Drying was continued to complete a total drying time of 24 hours in which the shelf temperature in the chamber was raised 1.0° C. per hour for the last 4 hours of the drying time culminating in a final temperature (shelf and product) of 44° C. While maintaining a chamber pressure of 0.06 mbar the vials were sealed and capped with aluminium seals.

Samples of the dehydrated product produced according to this example were stored at 45° C. for 14 days and the virus titre was determined as described above in Example 2. The residual moisture content of the product dehydrated according to the above procedure was determined to be approximately 1.0%. Following storage at 45° C. for 14 days samples of the product were found to have lost only a slight degree of virus potency and were suitable for producing useful vaccine material.

Example 4

The above procedure of Example 3 was followed for the production of stabilised RP by using RP virus culture instead of the PPR culture described in Example 3. The drying procedure similarly produced stabilised RP with relatively low loss of titre after being stored at 45° C. for 14 days.

What is claimed is:

1. A method of preserving a biologically-active material comprising a live virus or mycoplasma which method comprises the steps:
   (i) mixing an aqueous suspension of the biologically-active material with a sterile aqueous solution of trehalose to give a trehalose concentration in the mixture in the range of from 2.5 to 8% w/v;
   (ii) subjecting the mixture to primary drying, for 30 to 60 minutes, at a pressure of less than atmospheric pressure and at a temperature initially no greater than 37° C., and which is controlled not to fall to 0° C. or below and which finally is no greater than 40° C. to form a glassy porous matrix comprising glassy trehalose having a residual moisture content of not greater than 10% and containing, within the matrix, desiccated biologically-active material; and
   (iii) subjecting the glassy porous matrix of step (ii) to secondary drying for 10 to 30 hours at a pressure not greater than 0.1 mbar and at a temperature which finally is in the range of from 40 to 45° C. to form a trehalose matrix having a residual moisture content of not greater than 2% containing, within the matrix, desiccated biologically-active material.

2. A method according to claim 1, wherein secondary drying in step (iii) is carried out for 20 to 30 hours.

3. A method according to claim 2, wherein secondary drying is carried out for 15 to 17 hours at a temperature of about 37° C. and the temperature is, thereafter, raised gradually over the remaining secondary drying time to a final temperature in the range of from 40 to 45° C.

4. A method according to claim 1, wherein the primary drying in step (ii) is carried out at a pressure of not greater than 800 mbar.

5. A method according to claim 1, wherein the residual moisture content of the glassy trehalose matrix at the end of the primary drying in step (ii) is about 10%.

6. A method according to claim 1, wherein the residual moisture content at the end of the secondary drying in step (iii) is 1.0% or lower.

7. A method according to claim 1, wherein the live virus is selected from Rinderpest virus, Peste des Petits Ruminants virus, Measles virus, Mumps virus, Rubella virus, Yellow Fever virus, Polio virus and Newcastle Disease virus.

8. A method according to claim 7, wherein the live virus is Rinderpest virus or Peste des Petits Ruminants virus.

9. A method according to claim 1, wherein the mycoplasma is Contagious Bovine Pleuropneumonia mycoplasma.

* * * * *